US012751928B2

(12) United States Patent
Roussel-Maupetit et al.

(10) Patent No.: US 12,751,928 B2
(45) Date of Patent: Oct. 6, 2026

(54) PROLONGED-RELEASE PHARMACEUTICAL COMPOSITION FOR ORAL ADMINISTRATION OF SULTIAME

(71) Applicant: ADVICENNE, Paris (FR)

(72) Inventors: Caroline Roussel-Maupetit, St-Ismier (FR); Catherine Guittet, Arles (FR); Alexandra Guillermin, Grenoble (FR)

(73) Assignee: ADVICENNE, Paris (FR)

( * ) Notice: Subject to any disclaimer, the term of this patent is extended or adjusted under 35 U.S.C. 154(b) by 250 days.

(21) Appl. No.: 18/290,159

(22) PCT Filed: May 10, 2022

(86) PCT No.: PCT/EP2022/062635
§ 371 (c)(1),
(2) Date: Nov. 10, 2023

(87) PCT Pub. No.: WO2022/238401
PCT Pub. Date: Nov. 17, 2022

(65) Prior Publication Data

US 2024/0269083 A1 Aug. 15, 2024

(30) Foreign Application Priority Data

May 11, 2021 (EP) .................................... 21305609
Sep. 10, 2021 (EP) .................................... 21306243

(51) Int. Cl.
*A61K 9/50* (2006.01)
*A61K 31/54* (2006.01)

(52) U.S. Cl.
CPC .......... *A61K 9/5078* (2013.01); *A61K 9/5026* (2013.01); *A61K 9/5047* (2013.01); *A61K 31/54* (2013.01)

(58) Field of Classification Search
CPC ................................ A61K 31/54; A61P 25/08
See application file for complete search history.

(56) References Cited

U.S. PATENT DOCUMENTS

2003/0056896 A1* 3/2003 Jao ....................... A61K 9/0004 156/327
2011/0274762 A1* 11/2011 Fanara .................... A61P 25/16 424/490

FOREIGN PATENT DOCUMENTS

EP 3 517 103 7/2019

OTHER PUBLICATIONS

Written Opinion in International Application No. PCT/EP2022/062635, Aug. 31, 2022, pp. 1-9.
Unknown "Ospolot®" *Physician's Prescribing Information*, 2006, retrieved from the internet on Feb. 27, 2022, URL: https://www.pharmadoor.com.br/images/medicamentos/bulas/bula_ospolot.pdf, pp. 1-4.
Unknown "Australian Product Information—Ospolot® 50mg and 200mg Tablets" *Phebra*, 2021, retrieved from the internet on Feb. 27, 2022, URL: https://www.phebra.com/wp-content/uploads/2021/06/Ospolot-PI-V9.2.pdf, pp. 1-9.

* cited by examiner

*Primary Examiner* — Mark V Stevens
(74) *Attorney, Agent, or Firm* — SALIWANCHIK, LLOYD & EISENSCHENK

(57) ABSTRACT

The present invention relates to a prolonged-release pharmaceutical composition for oral administration of sultiame in the form of particles wherein the amount of sultiame is from 0.5 mg to 5.0 mg per particle, and the particles have a particle size of less than 5000 μm and comprise an outer layer providing prolonged-release of sultiame. The present invention also relates to the pharmaceutical composition of the invention for use for treating and/or preventing epilepsy.

18 Claims, 2 Drawing Sheets

PROLONGED-RELEASE PHARMACEUTICAL COMPOSITION FOR ORAL ADMINISTRATION OF SULTIAME

CROSS-REFERENCE TO RELATED APPLICATION

This application is the U.S. national stage application of International Patent Application No. PCT/EP2022/062635, filed May 10, 2022.

FIELD OF THE INVENTION

The present invention relates to a prolonged-release pharmaceutical composition for oral administration of sultiame and its use for preventing and/or treating epilepsy, in particular in children and in subjects with swallowing disorders.

TECHNICAL BACKGROUND

Epilepsy is a central nervous (neurological) system disorder that involves the repeated occurrence of sudden and transitory episodes of abnormal phenomena of motor, convulsion, sensory, autonomic, or psychic origin. The seizures are nearly always correlated with abnormal and excessive discharges in the brain which can be recorded by an electroencephalogram.

Epilepsy afflicts millions of people worldwide, and the disease is more common in children and elderly people (over 60 years old) than in adults.

To date, treatments for epilepsy include medicines called anti-epileptic drugs, surgery to remove a small part of the brain that's causing the seizures, a procedure to put a small electrical device inside the body that can help control seizures, or a special diet (ketogenic diet) that can help control seizures. Epilepsy is usually a lifelong condition and some patient need treatment for life.

Sultiame (also known as sulthiam(e) or sultiam) is an antiepileptic drug belonging to cyclic sulfonamide and having the following formula (I)

(I)

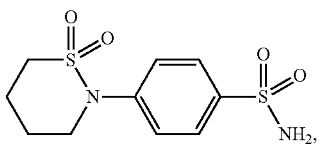

which is used, in particular in Europe, for managing seizures in certain types of epilepsy. The antiepileptic activity of sultiame is thought to mainly result from the inhibition of various subtypes of carbonic anhydrase (CA) enzymes. In particular, the blockade of cytosolic CA II seems to produce a degree of intracellular acidification sufficient to stabilize seizure-eliciting neurons. In addition, an inhibitory action on sodium channels possibly contributes to its antiepileptic efficacy (Dao et al., *Pharmacology Research & Perspectives,* 2020, Volume 8, Issue 1, e00558).

Sultiame is the first choice treatment in some countries, including in Europe, for Benign Epilepsy of Childhood with centrotemporal spikes (BECTS), a common (2% of school-age children) non-lesional epilepsy syndrome of childhood usually appearing between 3 and 12 years of age. BECTS is characterized by nocturnal oro-facial motor or sensory seizures, with or without bilateral propagation. The overall prognosis is good, with spontaneous disappearance of epilepsy at adolescence. Sultiame is also used for treating Continuous Spikes and Waves during slow Sleep (CSWS Epilepsy) that affects 0.2-0.5% of childhood epilepsies, and Refractory Depakine Epilepsy. Sultiame may also be used for treating the following disorders: Landau-kleffner, West, Lennox & Rett syndromes, acquired epilepsy-aphasia, atypical benign partial epilepsy, Temporal lobe epilepsy, Myoclonic and focal seizures.

Sultiame has been reported to be well tolerated and possibly more effective than other antiepileptic drugs commonly used in focal seizures, such as carbamazepine, gabapentine or levetiracetam (Dao et al., *Pharmacology Research & Perspectives,* 2020, Volume 8, Issue 1, e00558).

Sultiame is marketed under the tradename Ospolot® in Europe and in some other countries such as Israel, Argentina and Australia. Ospolot® is an immediate-release coated tablet comprising 50 mg or 200 mg of sultiame. Ospolot® is intended to be administered at least three times a day, usually at least four times a day, and the maintenance dose is in the range of 5 to 10 mg/kg body weight per day. Furthermore, a stabilization period of about 5-6 days is needed in order to achieve an effective plasma concentration. Of note, the dosage-form of Ospolot® does not allow a specific and precise dosage adjustment according the body weight and the responsiveness of the subject to the treatment, requires many intakes per day, requests a long initiation treatment period and can be difficult to swallow. Therefore, Ospolot® is a restrictive treatment that may be not appropriate for the lifestyle and the needs of certain patients such as children and the elderly people. Ospolot® is even considered as unsuitable for children under age of 6. Another shortcoming of the dosage form of Ospolot® is that it does not enable to provide a stable plasma concentration of sultiame. Indeed, one can observe high fluctuations in the sultiame plasmatic concentration overtime.

Besides, little is known about sultiame bioavailability. As of today, no broad pharmacokinetics study about Ospolot® has been performed. Very recently, Dao et al. (supra) showed that upon administration of single doses of Ospolot® under fasting conditions in healthy subjects, sultiame has a very strong affinity for erythrocytes. Such high affinity has an impact on the systemic bioavailability and the clearance of the drug. Thus, the conception of formulation and dosage regimen affording stable plasma level of sultiame able to promote a sustained therapeutic effect is a real challenge.

There is thus a need for developing a pharmaceutical composition comprising sultiame that addresses all of the drawbacks of Ospolot®.

SUMMARY OF THE INVENTION

The invention relates to a prolonged-release pharmaceutical composition for oral administration of sultiame in the form of particles, wherein:

- the amount of sultiame is from 0.5 mg to 5.0 mg per particle, and
- the particles have a particle size of less than 5000 μm and comprise an outer layer providing prolonged-release of sultiame.

Preferably, the particle size is determined by sieve analysis, as described further below.

In some embodiments, the particles comprise a core, a first layer comprising sultiame surrounding the core and the outer layer surrounding said first layer.

The prolonged-release pharmaceutical composition is preferably characterized by the following in vitro dissolution profile:

- no more than 20% of sultiame initially present in the composition is released within 1 h;
- from 30% to 60%, such as from 35% to 55% or from 40% to 50%, of sultiame initially present in the composition is released within 6 h; and
- at least 80% of sultiame initially present in the composition is released within 14 h, when the pharmaceutical composition is subjected to an in vitro dissolution assay at pH 6.8 according to European Pharmacopeia 01/2016:20903.

In some embodiments, the maximal particle size of the particle is at most 3000 μm, preferably of at most 2500 μm such as at most 2240 μm. In addition, from 70% to 100% by weight of the particles may have a particle size from 1000 μm to 3000 μm, particularly from 1400 μm to 2240 μm, more particularly from 1600 μm to 2240 μm, preferably from 1700 μm to 2240 μm. The amount of sultiame per particle is typically from 0.5 mg to 5.0 mg, preferably from 0.5 mg to 2.5 mg, more preferably from 1.5 to 2.5 mg.

In a particular embodiment, the prolonged-release pharmaceutical composition is such that the outer layer comprises at least one hydrophilic polymer and at least one hydrophobic polymer. The weight ratio of the hydrophobic polymer to the hydrophilic polymer may be from 1.5 to 3, preferably from 1.8 to 2.5.

In some embodiments, the hydrophilic polymer is polyvinylpyrrolidone and the hydrophobic polymer is ethylcellulose. The outer layer may further comprise a plasticizer and/or a surfactant. The first layer may further comprise a viscosity increasing agent and/or a surfactant. The core is typically made of an inert component preferably selected from the group consisting of polysaccharides, silica, calcium carbonate, magnesium carbonate, sugar, polyol, and mixtures thereof, preferably cellulose, microcrystalline cellulose, and mixtures thereof.

The Invention also relates to the use of the prolonged-release pharmaceutical composition as defined above in the prevention and/or the treatment of epilepsy in a subject. The prolonged-release pharmaceutical composition may be administered at most twice a day in the subject, such as twice a day, once a day or every two days.

The subject may be a child preferably an infant or a child under 7 years old and/or a subject with swallowing disorder. The prolonged-release pharmaceutical composition may be administered twice a day in the subject.

The mean daily dose of sultiame may be typically from 0.1 mg/kg to 10 mg/kg such as from 0.5 mg/kg to 10.0 mg/kg.

DETAILED DESCRIPTION OF THE FIGURES

DETAILED DESCRIPTION OF THE INVENTION

Figure 1:
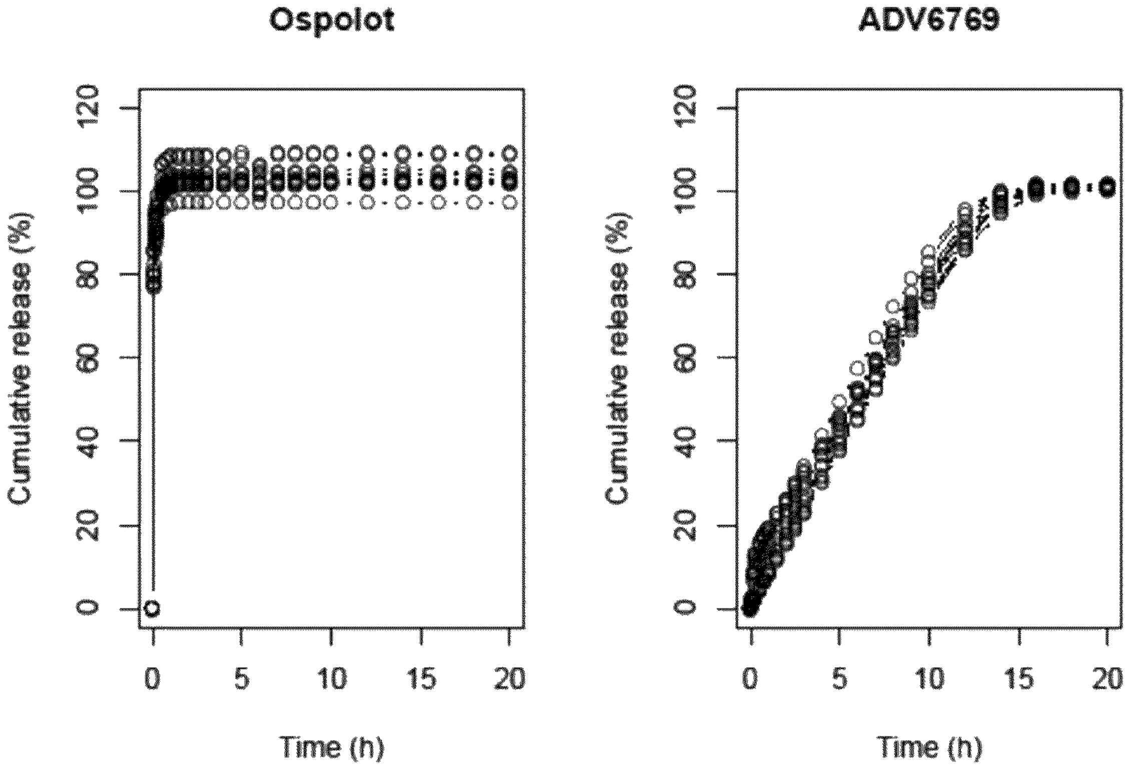
FIG. 1 (FIG. 1) shows the in vitro cumulative dissolution profiles of Ospolot® (left) and the composition according to the invention (ADV6769—right).
Figure 2:
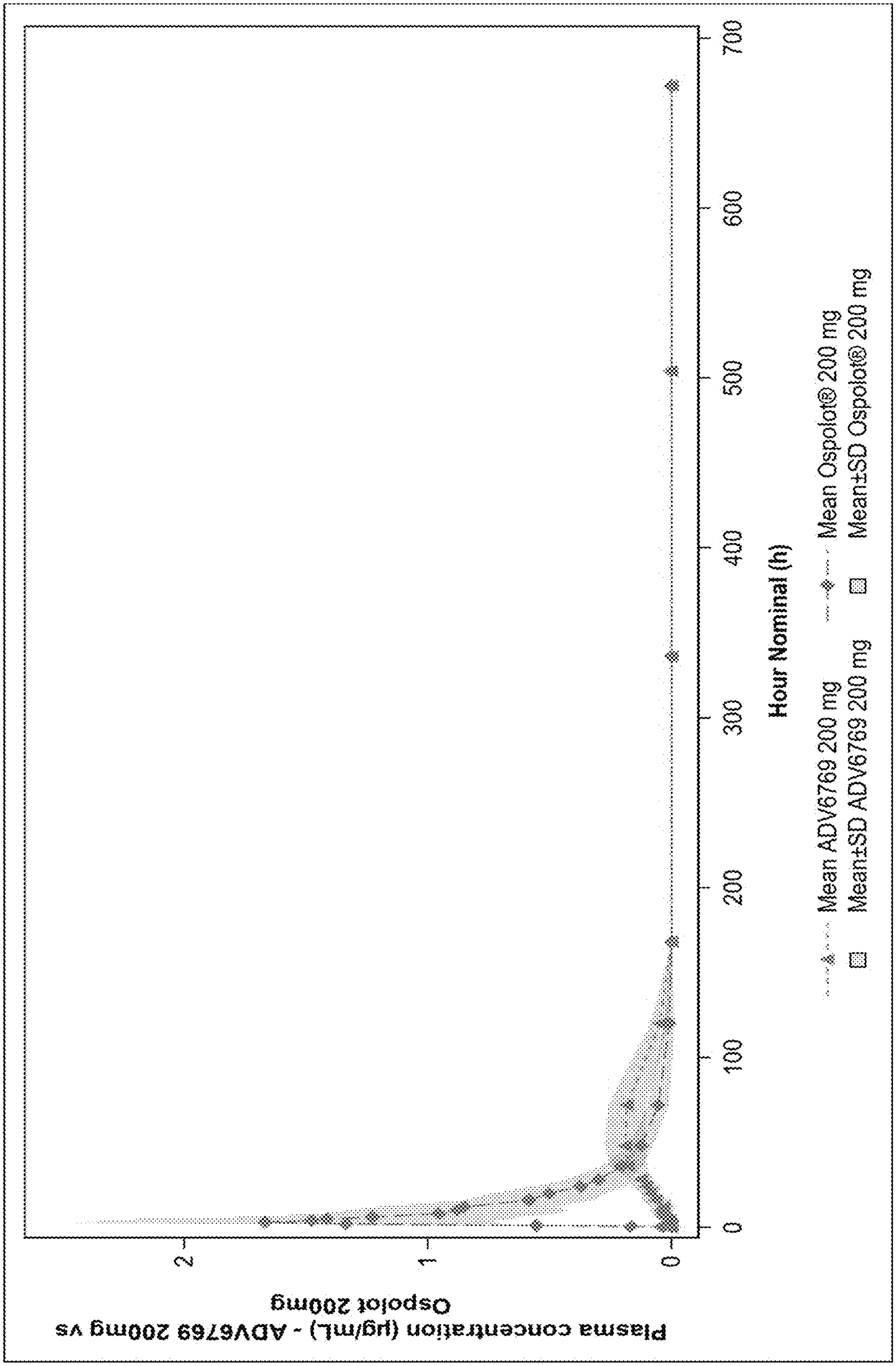
FIG. 2 (FIG. 2) shows the plasma pharmacokinetics profiles of Ospolotž and the composition according to the invention at a single dose of 200 mg.

The Inventors conceived a new pharmaceutical composition of sultiame. This pharmaceutical composition is based on small particles which provide a prolonged-release of sultiame.

As evidenced in the experimental section, the pharmaceutical composition of the invention provides an in vitro prolonged and regular release of sultiame over time, namely over at least 12 hours while the reference drug, Ospolot®, releases about 90% of the active ingredient within 30 min.

The in vitro dissolution profile of the composition of the invention was shown to be correlated with a prolonged release in vivo improving the pharmacokinetics of sultiame. Of note, the composition of the invention is characterized by a median Tmax of about 48 h, a mean Cmax of about 0.209 μg/mL when administered in an amount corresponding to 200 mg of sultiame under fasting condition to healthy adults. In contrast, Ospolot® provides a Tmax of about 2.5 h, a Cmax of about 1.763 μg/mL when administered in same conditions.

In view of these results, the pharmaceutical composition of the invention is expected to establish a stable and effective sultiame plasma concentration, with very low fluctuations, when administered twice or once a day. In contrast, Ospolot® provides a more fluctuating sultiame plasma concentration and shall be administered at least three or four times a day to provide an effective plasma level.

By virtue of its improved pharmacokinetics properties, the pharmaceutical composition of the invention is expected to provide a more stable plasma concentration of sultiame overtime while enabling to reduce the administration frequency as compared to the reference drug Ospolot®. In other words, the pharmaceutical composition of the invention is expected to provide a more effective and compliant treatment of epilepsy, with lower adverse effects, than the reference drug. Besides, the pharmaceutical composition of the invention displays several other advantages over the reference drug such as the possibility to finely adapt the dose to administer taking into account the body weight of the subject and his/her responsiveness to the treatment. Besides, due to its small dosage form easy to swallow the pharmaceutical composition of the invention is particularly suitable for administration to children, even under 6 years old and to subjects suffering from dysphagia.

Accordingly, the invention relates to a prolonged-release pharmaceutical composition for oral administration of sultiame in the form of particles, wherein:

- the amount of sultiame is from 0.5 mg to 5.0 mg per particle, and
- the particles have a size of less than 5000 μm and comprise an outer layer providing prolonged-release of sultiame.

The invention also relates to the use of such a pharmaceutical composition in the treatment of epilepsy, in particular in children or in subjects suffering from swallowing disorders.

General Definitions

In the context of the invention, by "pharmaceutically acceptable" is meant that which can be used in the preparation of a pharmaceutical composition, i.e. which is generally safe, non-toxic and neither biologically nor otherwise undesirable, and which is acceptable for veterinary use as well as for human pharmaceutical use.

In the context of the invention, by "pharmaceutically acceptable salt" of a compound is meant a salt which is pharmaceutically acceptable as defined herein and which has the desired pharmacology activity of the parent compound.

Pharmaceutically acceptable salts notably comprise:

(1) the addition salts of the compound of interest obtained with pharmaceutically acceptable inorganic acids such as hydrochloric, hydrobromic, phosphoric, sulfuric and similar acids; or with pharmaceutically acceptable organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic and similar acids; and (2) the addition salts of the compound of interest obtained with a pharmaceutically acceptable organic base such as lysine, arginine and similar; or with a pharmaceutically acceptable inorganic base such as sodium hydroxide, calcium hydroxide and similar.

In the context of the invention, the term "effective amount" refers to a quantity of an active ingredient effective, at dosages and for periods of time necessary, to achieve the desired therapeutic or prophylactic result, i.e. an amount effective for preventing, removing or reducing the deleterious effects of the disease. It is obvious that the quantity to be administered can be adapted by the skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "treatment", "treat" or "treating" refers to any act intended to ameliorate the health status of patients such as therapy. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease. In the context of epilepsy, these terms refer to any act intended to eradicate the disease or to avoid, minimize or reduce the seizure frequency and severity.

As used herein, the term "preventing" or "prevention" refers to any act intended to avoid the onset of a disease such as prophylaxis and retardation of the disease.

In the context of the invention, the terms "subject", "individual" or "patient" are interchangeable and refer to an animal, preferably to a mammal, even more preferably to a human. As defined further below, the subject is of need of sultiame therapy. In particular, the subject suffers from epilepsy. Said subject may be of any gender and any age. Preferably, the subject is selected from children, especially those under 12 years, preferably under 6 years old such as infants and toddlers, and subjects having swallowing disorders (namely dysphagia). Swallowing disorders can have various etiologies. Subjects with swallowing disorders encompass, without being limited to, elderly subjects, subjects suffering from certain neurological disorders, such as neurodegenerative or neurodevelopmental disorders, subjects suffering from lesions in the swallowing apparatus e.g. subjects who underwent surgical resection of the oropharynx/larynx, or radiation injury, and subjects who underwent anterior cervical spine surgery.

In the context of the invention, "a prolonged-release dosage form or composition" refers to a composition which releases the active ingredient over an extended period of time of at least 4 hours, in particular from 6 h to 24*h* in an in vitro dissolution assay as described in the European Pharmacopeia. In contrast, "an immediate release dosage form or composition" releases more than 80% of the active ingredient within 45 minutes in an in vitro dissolution assay as described in the European Pharmacopeia.

In the context of the invention, the term "particle" or "particle dosage form" refers to a solid dosage form composed of a plurality of individual particles, each particle being a small mass that contains an active ingredient (herein sultiame or a pharmaceutically acceptable salt thereof) together with one or several pharmaceutically acceptable excipients. The term "particle dosage form" includes, without being limited to, bead dosage form and granule dosage form.

In the context of the invention, the term "bead" or "bead dosage form" refers to a particle solid dosage form, in particular in the shape of a sphere. The bead generally comprises a core (e.g. an inert core), typically a spherical core coated with one or multiple layers such as a drug-containing layer and a controlled-release layer (e.g. a prolonged-release layer). Such coated beads (also known as multilayer beads) may be prepared by any conventional process known by the skilled artisan, which include for instance wet-mass extrusion, spheronization, layering or spray-drying, e.g. on an inert core, and/or coating.

In the context of the invention, the term "granule" or "granule dosage form" refers to a particle solid dosage form, in particular in the shape of a sphere, that is prepared by granulation e.g. though high-shear granulation and melt-granulation processes. Granules can result from granulating active ingredient with polymers and other excipients to generate modified release granules such as prolonged-release granules.

In the context of the invention, the "particle size" and more generally the "particle size distribution" is determined by sieve analysis, typically by using a sieve stack, e.g. several sieves, e.g. from 3 to 8 sieves arranged in a stack with the mesh size increasing from bottom to top.

The Pharmaceutical Composition of the Invention

As mentioned above, the invention relates to a prolonged-release pharmaceutical composition for oral administration of sultiame in the form of particles, wherein:

the amount of sultiame is from 0.5 mg to 5.0 mg per particle, and the particles have a particle size of less than 5000 μm and comprise an outer layer providing prolonged-release of sultiame.

In the context of the invention, the term sultiame includes sultiame base, pharmaceutically acceptable salts thereof such as sodium sultiame, and solvates thereof including hydrates. According to a particular embodiment, sultiame is sultiame base having the following formula:

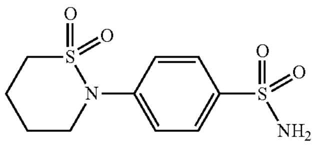

The particles of the invention have a size at most 5000 μm e.g. of at most 4000, 3500, 3000 or 2500 μm.

In the context of the invention, "the particles have a size of at most 5000 μm" means that at least 95% of the particles, such as at least 96%, 97%, 98%, 99%, 99.5%, 99.8%, or 99.9% of the particles of the pharmaceutical composition have a size of at most 5000 μm, the percentage being expressed by weight with respect to the total weight of the particles.

In a particular embodiment, the particles of the invention have a size from 1000 μm to 5000 μm.

In advantageous embodiments, the particles of the invention have a maximal particle size of at most 5000 μm, advantageously of at most 3500 μm, such as 3000 μm, 2800 μm, 2600 μm and preferably of at most 2500 μm, or of at most 2240 μm.

The size distribution in the particles according to the invention can be determined by any size distribution analysis known by the skilled artisan. Preferably, the particle size distribution of the particles can be determined by sieve analysis, typically by using a sieve stack, e.g. several sieves, e.g. from 3 to 8 sieves arranged in a stack with the mesh size increasing from bottom to top.

Sieve analysis is well known by the skilled artisan. For instance, one can use any commercially available stainless sieve stack equipped with an appropriate mechanical shaker Typically, the sample to analyze is placed on the sieve at the top of the stack and subjected to vertical movement (vibratory sieving) and/or horizontal motion (horizontal sieving) by the means of a mechanical shaker. During this process the particle of the sample are compared with the apertures of every single sieve. The probability of a particle passing through the sieve mesh is determined by the ratio of the particle size to the sieve openings, the orientation of the particle and the number of encounters between the particle and the mesh openings. The appropriate sieve analysis method depends on the degree of fineness of the sample. Sieve analysis method is the preferred method for the size range between 20 μm and 125 mm, as in the context of the invention.

In the context of the invention, the "maximal particle size" is measured by sieve analysis and refers to the size of the largest particle(s), i.e. the mesh diameter of the first sieve that retains particles.

In another embodiment, the particles of the invention have a minimal particle size of at least 1000 μm, advantageously of at least 1200 μm, more advantageously of at least 1400 μm.

In the context of the invention, the "minimal particle size" is measured by sieving stack and refers to the size of the smallest particle, i.e. the mesh diameter of the last sieve that retains particles.

In some embodiments, from 70% to 100% by weight of the particles have a particle size from 1000 to 2500 μm, in particular 1400 μm to 2240 μm, more particularly from 1600 μm to 2240 μm, preferably from 1700 μm to 2240 μm.

In particular, from 80% to 100% by weight of the particles have a particle size from 1000 to 2500 μm, in particular from 1400 μm to 2240 μm, in particular from 1600 μm to 2240 μm, preferably from 1700 μm to 2240 μm.

Preferably, from 90% to 100% by weight of the particles have a particle size from 1000 to 2500 μm, in particular from 1400 μm to 2240 μm, more particularly from 1600 μm to 2240 μm, preferably from 1700 μm to 2240 μm. The percentages are measured by weight in relation to the total weight of the particles. According to the invention, the particle size allows an easy administration of the composition of the invention, in particular in children and in subjects having swallowing disorders.

Advantageously, in the composition of the invention, the amount of sultiame per particle is from 0.5 mg to 5.0 mg, preferably from 0.5 mg to 2.5 mg, more preferably from 1.5 to 2.5 mg.

According to the invention, the amount of sultiame per particle allows adaptation of the doses to the patient, in particular according to the weight and/or the age of the patient, the responsiveness of the patient to the treatment, and the stage of the disease. In the art, the recommended maintenance dose of sultiame is in the range of 5 to 10 mg/kg body weight per day and the dose for initiating the treatment is about 2.5 mg/kg body weight per day. The dosage form of the invention thus allows the administration of the adequate doses even in the youngest patients such as children of less than 6 years old including toddlers and even infants.

The pharmaceutical composition of the invention provides a prolonged-release of sultiame. Such a prolonged-release of sultiame can be evidenced by in vitro dissolution assay typically performed according to the European Pharmacopeia, 01/2016:20903.

Typically, the pharmaceutical composition of the invention is such that no more than 65% of sultiame initially present in the composition is released within 6 h, when the composition is subjected to an in vitro dissolution assay according to the European Pharmacopeia 01/2016:20903, with the following conditions:

Apparatus: paddle (Apparatus 2),
Temperature: 37° C.,
Dissolution medium: phosphate buffer 0.05 M at pH 6.8,
Stirring rate: 100 rpm.

Typically, 10 particles (e.g. 10 coated beads) of the pharmaceutical composition are placed in 900 mL of dissolution medium, at pH 6.8 at 37° C., under a stirring rate of 100 rpm. The sultiame release in the dissolution medium overtime is quantified by UV detection (typically at 245 nm).

In a particular embodiment, the pharmaceutical composition is such that at least 70%, in particular at least 75%, 80%, 85% or 90% of sultiame initially present in the composition is released within 14 hours when the composition is subjected to an in vitro dissolution assay as defined above.

In another embodiment, the pharmaceutical composition is such that no more than 25%, in particular no more than 20% of sultiame initially present in the composition is released within 1 hour when the composition is subjected to an in vitro dissolution assay as defined above.

In a preferred embodiment, the pharmaceutical composition is such that:

no more than 20% of sultiame initially present in the composition is released within 1 h,
from 30% to 60%, such as from 35% to 55% or from 40% to 50%, of sultiame initially present in the composition is released within 6 h, and
at least 80% of sultiame initially present in the composition is released within 14 h, when the composition is subjected to an in vitro dissolution assay as defined above.

As evidenced by the example section, the exemplified composition has an in vitro dissolution profile which is independent of the pH, more preferably which is essentially the same at pH 6.8 and at pH 1.2 or 4.5.

Accordingly, in some embodiments, the composition of the invention meets the same in vitro dissolution specifications at pH 1.2 and 4.5 as those described above at pH 6.8.

In a particular embodiment, the pharmaceutical composition of the invention is pH-independent.

In some further embodiments, the prolonged-release pharmaceutical composition does not release a significant amount of the active ingredient in the stomach. Typically, the prolonged-release composition of the invention releases less than 15%, preferably less than 10% or 5% of sultiame initially present in the composition within one hour when the pharmaceutical composition is subjected to an in vitro dissolution assay at pH 1.0.

As mentioned above, the improved in vitro dissolution profile of the invention is expected to be correlated with an improved pharmacokinetics profile in vivo. Such a fact can be evidenced by standardized pharmacokinetics study in vivo, e.g. as shown in the example section.

As exemplified, the composition of the invention is characterized by a significant increase in median Tmax, and decrease in mean Cmax as compared to Ospolot® tablet, when both products are administered at the same dosage, in a single dose, under fasting conditions, to healthy adults.

Accordingly, in some further embodiments, the pharmaceutical composition of the invention is characterized by a median Tmax of at least 36 hours, e.g. from 36 h to **72*h***, preferably of about 48 hours, when orally administered in one daily dose of 200 mg to healthy adult subjects under fasting conditions.

In some other embodiments, the pharmaceutical composition of the invention is characterized by a mean Cmax of less than 0.3 μg/mL, e.g. from 0.1 to 0.3 μg/mL, when orally administered in one daily dose of 200 mg to healthy adult subjects under fasting conditions.

In a particular embodiment, the pharmaceutical composition of the invention is characterized by a mean $AUC_{0-4}$ of less than 22 h*μg/mL, preferably less than 15 h*μg/mL, e.g. from 10 to 15 h*μg/mL, when orally administered in one daily dose of 200 mg respectively, to healthy adult subjects under fasting conditions.

In a particular embodiment, the pharmaceutical composition of the invention, when orally administered in one daily dose of 200 mg (number of particles sufficient to reach a dose of 200 mg) to healthy adult subjects under fasting conditions, is adapted to provide a pharmacokinetic profile for sultiame having the following features:

(i) a median $T_{max}$ of at least 36 hours, preferably of about 48 hours;

(ii) a mean $C_{max}$ of less than 0.3 μg/mL, e.g. from 0.1 to 0.3 μg/mL; and (iii) a mean $AUC_{0-4}$ of less than 22 h*μg/mL, preferably less than 15 h*μg/mL, e.g. from 10 to 15 h*μg/mL.

The Tmax, the Cmax and the AUC0 h-t refer to plasma data and are determined based on the sultiame plasma concentration versus time curve.

According to the present invention, for a given sultiame-containing composition, the sultiame plasma concentration versus time curve may be determined by following plasma sultiame concentration over a desired period, e.g. during at least 7 days such as about 8 days or about 28 days after a single oral intake of an amount of the composition corresponding to a dosage of 200 mg of sultiame.

The single oral administration of the said sultiame-containing composition is performed in fasting conditions i.e. without food and not close to mealtime (i.e. in general, approximately 10 h after meal) since food ingestion may modify the absorption rate of sultiame in the gastrointestinal tractus. The Cmax and Tmax values refer to the maximum sultiame plasma concentration and the time to reach it, respectively, after the oral administration of a single dose of the composition of interest. In other words, Tmax and Cmax refer to the characteristics of sultiame plasma concentration peak observed after the oral intake of a single dose of the composition of interest. The $AUC_{0-4}$ corresponds to the area obtained by integration of the sultiame plasma concentration versus time over the interval [0 h-t], the point “0 h” referring to the oral intake of the composition of interest and the point “t” refers to the last time for which plasma concentration of sultiame is quantified.

The mean $C_{max}$, median $T_{max}$ and mean $AUC_{0-4}$ for sultiame may be determined from raw individual pharmacokinetic data in plasma from a statistically number of subjects, by well-known statistical methods of the prior art. The pharmacokinetic studies can be performed as described in the Example section.

Thanks to this prolonged release, the formulation of the invention is expected to provide a stable plasma concentration of sultiame when administered at most twice a day, preferably once a day, in a maintenance treatment.

Of note, the pharmaceutical composition of the invention may enable a reduced frequency of administrations as compared to the reference drug, which improves the compliance to sultiame treatment.

The Pharmaceutical Composition

As defined above, the invention relates to a prolonged-release pharmaceutical composition for oral administration of sultiame in the form of particles, wherein:

the amount of sultiame is from 0.5 mg to 5.0 mg per particle, and the particles have a particle size of less than 5000 μm and comprise an outer layer providing prolonged-release of sultiame.

Advantageously, the composition of the invention is a bead dosage form or a granule dosage form, in particular a bead dosage form. More advantageously, the composition of the invention is a multilayered bead dosage form.

In a preferred embodiment, the composition of the invention is in the form of a plurality of coated beads, each coated bead comprises a core, a first layer comprising sultiame surrounding the core and the outer layer surrounding said first layer.

In the context of the invention, the terms “core”, “inert core” or “neutral core” refer to an inert substrate, in particular in the shape of a sphere, consisting of inert excipient (s). Therefore, the core does not comprise any active ingredient including sultiame. In addition, the core does not exhibit any pharmacological activity nor interact with sultiame in a way, which may adversely affect its stability and/or effectiveness.

The core, also called inert core, typically consists of at least one inert pharmaceutical excipient selected from the group consisting of polysaccharides, such as cellulose, or microcrystalline cellulose, silica, calcium carbonate, magnesium carbonate, sugar (such as lactose or sucrose), polyol (such as mannitol, sorbitol, or maltitol), and mixtures thereof, preferably cellulose, microcrystalline cellulose, and mixtures thereof.

In a preferred embodiment, the core is devoid of sucrose, and more preferably is devoid of any disaccharide or monosaccharide.

According to the invention, the particle size of the core is selected so that the desired particle size of the composition of the invention may be obtained while comprising the desired amount of sultiame. Advantageously, the core has a particle size ranging from 600 μm to 1000 μm, in particular 700 μm to 850 μm. The size (and more precisely the size distribution of the starting core particles) can be determined by sieve analysis, e.g. as disclosed above for the final particles of the invention.

According to the invention, the core advantageously accounts for 5% to 15% by weight of the particle, the percentage being expressed by weight as compared to the total weight of the particle.

According to the invention, the particle, in particular the bead, may comprise a first layer which is a drug-containing layer comprising sultiame.

According to the invention, the amount of sultiame in the first layer is advantageously from 0.5 mg to 5.0 mg, preferably from 0.5 mg to 2.5 mg, more preferably from 1.5 to 2.5 mg.

Advantageously, sultiame in the first layer accounts for 60% to 85% by weight of the total weight of the first layer.

The amount of sultiame in the composition of the invention is typically from 45% to 60%, by weight of the total weight of the composition of the invention.

The first layer may also comprise one or several pharmaceutically acceptable excipients. The one or more excipients can be selected from the group consisting of binders, surfactants, diluents, viscosity increasing agent, and mixtures thereof. The pharmaceutically acceptable excipients that may be used are, in particular, described in the Handbook of Pharmaceuticals Excipients, American Pharmaceutical Association (Pharmaceutical Press; 9th revised edition, 2020). In some embodiments, the first layer further comprises a surfactant and/or a viscosity increasing agent.

Examples of surfactants include, without being limited to, glyceryl monooleate, sodium lauryl sulfate, lauric acid, myristyl alcohol, glyceryl monooleate, polyoxyethylene alkyl ethers, polyoxyethylene and/or pegylated and/or hydrogenated castor oil derivatives, polyoxyethylene sorbitan fatty acid esters such as polysorbate 80, polyoxyethylene stearates, polyoxylglycerides, sorbitan esters, and combination thereof.

According to the invention, a preferred surfactant is pegylated hydrogenated castor oil or polysorbate 80, preferably pegylated hydrogenated castor oil.

Examples of viscosity increasing agents include, without being limited to, acacia, agar, alginic acid, bentonite, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, guar gum, hectorite, hydrogenated vegetable oil type I, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, polydextrose, polyethylene glycol, poly (methylvinyl ether/maleic anhydride), polyvinyl alcohol, potassium chloride, povidone, propylene glycol alginate, saponite, sodium alginate, sodium chloride, starch, stearyl alcohol, sucrose, tragacanth, and xanthan gum.

According to the invention, the viscosity increasing agent is preferably hydroxypropyl methyl cellulose (HPMC), or povidone, more preferably HPMC.

Advantageously, the first layer comprises a surfactant such as pegylated hydrogenated castor oil and a viscosity increasing agent such as HPMC.

The surfactant may account for 5% to 10% by weight of the total weight of the first layer and the viscosity increasing agent may account for 10% to 25% by weight of the total weight of the first layer.

The excipient(s) present in the first layer typically account(s) for 15 to 40%, by weight in relation to the total weight of the first layer.

According to the invention, the first layer advantageously accounts for 60% to 80% by weight of the particle, the percentage being expressed by weight as compared to the total weight of the particle.

According to the invention, the particle, in particular the bead, comprises an outer coating layer providing prolonged-release of sultiame.

The outer coating layer typically comprises controlled release agents that provide prolonged-release of sultiame. Examples of controlled release agents include, but are not limited to, hydrophilic polymers, hydrophobic polymers and wax materials.

In a preferred embodiment, the outer coating layer comprises at least one hydrophilic polymer and at least one hydrophobic polymer, as controlled release agents. In particular, in the context of the invention, the balance between the hydrophilic and hydrophobic polymers defines the release of the sultiame. Indeed, the more hydrophobic the outer coating layer is, the slower the release of sultiame will be. Therefore, the weight ratio of the hydrophobic polymer to the hydrophilic polymer should be chosen with care by the one skilled in the art. Advantageously the weight ratio of the hydrophilic polymer to the hydrophobic polymer is from 1.5 to 3, preferably from 1.8 to 2.5 such as 1.9 to 2.4.

Advantageously, in the outer coating layer, the hydrophilic polymer is selected from the group consisting of polyvinylpyrrolidone (povidone), hydroxypropylmethylcellulose, hydroxypropylcellulose, sodium carboxymethylcellulose, carboxymethylcellulose calcium, ammonium alginate, sodium alginate, potassium alginate, calcium alginate, propylene glycol alginate, alginic acid, polyvinyl alcohol, carbomer, potassium pectate, potassium pectinate, and mixtures thereof.

In particular, the hydrophilic polymer is polyvinylpyrrolidone.

Advantageously, the amount of hydrophilic polymer in the outer coating layer is from 50% and 70%, by weight in relation to the total weight of the outer layer. The hydrophilic polymer in the outer layer may account from 5% and 20%, by weight in relation to the total weight of the composition of the invention.

Advantageously, in the outer layer, the hydrophobic polymer is selected from the group consisting of ethylcellulose, hydroxyethylcellulose, ammonio methyacrylate copolymer (Eudragit® RL or Eudragit® RS), methyacrylic acid copolymers (Eudragit® L or Eudragit® S), methacrylic acid-acrylic acid ethyl ester copolymer (Eudragit® L 100-5), methacrylic acid esters neutral copolymer (Eudragit® NE 30D), dimethylaminoethylmethacrylate-methacrylic acid esters copolymer (Eudragit® E 100), vinyl methyl ether/maleic anhydride copolymers, their salts and esters (Gantrez®), and mixtures thereof.

In particular, the hydrophobic polymer is ethylcellulose.

Preferably, the hydrophobic polymer is ethylcellulose having a viscosity range of 6 mPa·s to 22 mPa·s, in particular 6 mPa·s to 11 mPa·s, such as 6 mPa·s to 8 mPa·s. The viscosity of ethylcellulose can be determined as described in the ethylcellulose monograph of the European Pharmacopeia by capillary viscometer method. Typically, 5 g of dry ethylcellulose is dissolved in 95 g of a mixture comprising ethanol (96%)/toluene at a weight ratio of 20/80. The viscosity is then determined at 25° C. by using a capillary viscometer.

Advantageously, the amount of hydrophobic polymer in the outer coating layer is from 20% and 40%, by weight in relation to the total weight of the outer layer.

The amount of hydrophobic polymer in the composition of the invention is generally from 3% to 10%, by weight in relation to the total weight of the composition of the invention.

Advantageously, the outer coating layer further comprises a further excipient selected from the group consisting of plasticizer, surfactant, colorants or pigments, glidants, flavors, viscosity increasing agents, and mixtures thereof. The pharmaceutically acceptable excipients that may be used are, in particular, described in the Handbook of Pharmaceuticals Excipients, American Pharmaceutical Association (Pharmaceutical Press; 6th revised edition, 2009).

Advantageously, the further excipient of the outer coating layer is a mixture of at least a plasticizer and a surfactant.

Examples of plasticizer include, without being limited to, acetyltributyl citrate, acetyltriethyl citrate, benzyl benzoate, castor oil, chlorbutanol, dextrin, dibutyl sebacate, glycerin, glycerin monostearate, mannitol, mineral oil, palmitic acid, petrolatum, polyethylene glycol, propylene glycol, pyrrolidone, sorbitol, stearic acid, triacetin, tributyl citrate, triethanolamine, and combination thereof.

The plasticizer is preferably castor oil. The plasticizer may account for 1% to 10% by weight of the total weight of the coating.

Examples of surfactants include, without being limited to, all the surfactants that are recited above.

A preferred surfactant is pegylated hydrogenated castor oil. The surfactant in the coating may account for 1% to 8% by weight of the total weight of the coating.

The weight ratio of the plasticizer to the surfactant in the coating may be from 1 to 2.

Advantageously, the outer coating layer is devoid of active ingredient, i.e. is devoid of sultiame. More advantageously, the outer coating layer is devoid of sultiame and comprises polyvinylpyrrolidone and ethyl cellulose as release controlling agents together with castor oil as plasticizer and pegylated hydrogenated castor oil as surfactant.

According to the invention, the outer coating layer advantageously accounts for 15% to 25% by weight of the particle, the percentage being expressed by weight as compared to the total weight of the particle.

In an advantageous embodiment of the invention, the pharmaceutical composition is in the form of multilayered beads having a particle size from 1500 μm to 2500 μm (preferably a maximal particle size of no more than 3000 μm), each bead comprising, or consisting of:

A spherical core;

A first layer surrounding the spherical core comprising sultiame in an amount from 0.5 mg to 2.5 mg, and optionally at least one excipient selected from a binding agent, a surfactant, a viscosity increasing agent and combinations thereof; and An outer layer surrounding the first layer, which is devoid of sultiame and comprises at least one hydrophobic polymer such as ethylcellulose and at least one hydrophilic polymer such as polyvinylpyrrolidone (PVP) in a weight ratio hydrophilic polymer to hydrophobic polymer from 1.5 to 3, and optionally at least one further excipient such as a plasticizer and/or a surfactant.

Preferably, the spherical core accounts for 5% to 15%, the first layer accounts for 60% to 80%, and the outer coating layer accounts for 15% to 25%; the percentages being expressed by weight as compared to the total weight of the particle. Sultiame preferably accounts for 45% to 60% by weight to the total weight of the particle.

In an advantageous embodiment of the invention, each bead comprises or consists of:

A spherical core preferably made of microcrystalline cellulose;

A first layer surrounding the spherical core comprising sultiame in an amount from 0.5 mg to 2.5 mg, a viscosity increasing agent such as hydroxypropyl methyl cellulose (HPMC) and a surfactant such as pegylated hydrogenated castor oil; and An outer layer coating devoid of sultiame and comprising hydrophobic polymer such as ethylcellulose and hydrophilic polymer such as polyvinylpyrrolidone (PVP) in a weight ratio hydrophobic polymer to hydrophilic polymer from 1.5 to 3, a plasticizer such as castor oil and a surfactant such as pegylated hydrogenated castor oil.

Preferably, the spherical core accounts for 5% to 15%, the first layer accounts for 60% to 80% with sultiame present in the first layer accounting for 45% to 60%, and the outer coating layer accounts for 15% to 25%; the percentages being expressed by weight as compared to the total weight of the particle.

In another advantageous embodiment of the invention, said bead comprises or consists of:

A spherical core made of microcrystalline cellulose and preferably having a particle size ranging from 650 μm to 900 μm, preferably from 710 μm to 850 μm;

A first layer surrounding the spherical neutral core comprising sultiame in an amount from 0.5 mg to 2.5 mg, hydroxypropyl methyl cellulose (HPMC) as a viscosity increasing agent and pegylated hydrogenated castor oil as surfactant; and An outer layer coating devoid of sultiame and comprising ethylcellulose as hydrophobic polymer and polyvinylpyrrolidone (PVP) as hydrophilic polymer in a weight ratio ethylcellulose to PVP from 1.5 to 3, castor oil as plasticizer and pegylated hydrogenated castor oil as surfactant.

Preferably, from 70% to 100% by weight of the particles have a particle size from 1400 μm to 2240 μm.

Preferably, the spherical core accounts for 5% to 15%, the first layer accounts for 60% to 80% with sultiame present in the first layer accounting for 45% to 60%, and the outer coating layer accounts for 15% to 25%; the percentages being expressed by weight as compared to the total weight of the particle.

In the above embodiments, said bead may be further characterized in that:

the spherical core is made of microcrystalline cellulose and accounts for 5% to 10% by weight of the total weight of the bead, sultiame is present in the first layer only and accounts for 50% to 60% by weight of the total weight of the bead, and/or HPMC present in the first layer accounts for 10% to 15% by weight of the total weight of the bead, and/or pegylated hydrogenated castor oil in the first layer accounts for 3% to 8% by weight of the total weight of the bead, and/or Ethylcellulose in the coating accounts for 2% to 10% by weight of the total weight of the bead, and/or castor oil in the coating accounts for 0.5% to 2% by weight of the total weight of the bead, and/or povidone in the coating accounts for 5% to 20% by weight of the total weight of the bead, and/or pegylated hydrogenated castor oil in the coating accounts for 0.1% to 2% by weight of the total weight of the bead.

Process of Preparation

The pharmaceutical composition in accordance with this invention can be prepared by common methods well known to those skilled in the art of manufacturing drug compositions.

In particular, when the particles according to the invention are in the form of coated beads, they may be prepared by any conventional process known by the skilled artisan, which include for instance wet-mass extrusion, spheronization, spray-drying, layering and/or coating. Besides, when the particles of the invention are in the form of granule, they may be prepared by any granulation method known by the one skilled in the art, such as though high-shear granulation or melt-granulation processes.

When the pharmaceutical composition is in the form of coated beads, said beads may be typically prepared by carrying out the following steps:

Step (a) Preparing the suspension or solution to be coated as the drug-containing layer;

Step (b) Coating a core with the suspension prepared in step (a);

Step (c) Optionally, sieving the particles

Step (d) Preparing the suspension for the outer layer;

Step (e) Coating particles obtained after step (b) or (c) with the suspension prepared in step (d); and Step (f) Sieving for recovering the particles having a maximal particle size of at most than 5000 μm, in particular at most 3500 μm, 3000 μm or 2500 μm, advantageously at most 2240 μm.

According to the invention, step (a) typically comprises the preparation of a suspension to be sprayed as the drug-containing layer. The suspension may be prepared by means known by the one skilled in the art. In particular, the suspension comprises all the components of the first layer, i.e. the sultiame and optionally the further excipient(s) such as the surfactant and the increasing viscosity agent in an appropriate solvent such as water or hydro-alcoholic solution. The composition of the first layer is in particular as defined above.

In a particular embodiment, step (a) may be carried out by incorporating sultiame and the further excipient in the solvent under high speed stirring.

According to the invention, step (b) and (e) are carried out by means known by the one skilled in the art. In particular, the coating steps (b) and (e) may be carried out in solid pans, side vented pans, fluid bed machines, fully perforated drums, and continuous coaters. Advantageously, steps (b) and (e) are carried out in a fluidized bed.

According to the invention, steps (c) and (f) are carried out by means known by the one skilled in the art. In particular, steps (c) and (f) are carried out by sieving, typically with vibrating sieves. In some embodiments, step (c) is performed so as to recover pre-coated particles having a particle size lower than 5000 μm, preferably lower than 3000 μm.

According to the invention, step (d) advantageously relates to the preparation of a suspension to be sprayed as the prolonged release outer layer. The suspension may be prepared by means known by the one skilled in the art. In particular, the suspension comprises all the components of the outer layer, i.e. the release controlling agents and optionally the further excipients (such as surfactant and plasticizer) in an appropriate solvent such as water, alcohol (e.g.isopropanol) or other organic solvents (e.g. acetone) and combinations thereof. The composition of the outer layer is in particular as defined above.

Conditions (temperature, concentration, solvents, reactants, equivalents of the reactants) described above for each step may be adjusted by the skilled artisan using his/her general background in galenic.

Uses

Another aspect of the invention is the pharmaceutical composition of the invention for use as a medicament, in particular for use for treating and/or preventing epilepsy.

In particular, the invention is directed to the pharmaceutical composition of the present invention for use for treating and/or preventing epilepsy in a subject.

In an embodiment, the invention is directed to a method for treating and/or preventing epilepsy in a subject in need thereof, the method comprising a step of administering to the subject an effective amount of the pharmaceutical composition of the invention.

In an embodiment, the invention is directed to the use of the pharmaceutical composition of the invention for the manufacture of a medicament for treating and/or preventing epilepsy in a subject.

In the context of the invention, the epilepsy to be treated or prevented is advantageously selected from the group consisting of Benign Epilepsy of Childhood with Centrotemporal Spikes (BECTS), Continuous Spikes and Waves during slow Sleep (CSWS Epilepsy), Refractory Depakine Epilepsy, Landau-kleffner, West, Lennox & Rett syndromes, acquired epilepsy-aphasia, atypical benign partial epilepsy, temporal lobe epilepsy, myoclonic and focal seizures. More advantageously, the epilepsy to be treated or prevented is Benign Epilepsy of Childhood with Centrotemporal Spikes (BECTS).

According to the invention, the composition is to be administered via oral route. The dosage can be determined according to the criteria generally taken into account in the establishment of a treatment adapted to a patient such as, for example, the age or the body weight of the patient, the seriousness of his/her general condition, the tolerance to the treatment and the adverse effects noted. In particular, according to the invention, the number of particles to be administered per day and per intake can be determined according to the criteria generally taken into account for treating epilepsy, adapted to the subject.

The daily dose of sultiame to be administered may be from 0.5 mg/kg body weight to 10.0 mg/kg body weight, e.g. 0.5 mg/kg to 1.0 mg/kg, from 1.0 to 1.5 mg/kg or 1.5 mg/kg to 6.0 mg/kg. In particular, the daily initial dose to be administered (at the beginning of the treatment) is advantageously from 1.0 mg/kg body weight to 3.5 mg/kg body weight, e.g. 2.5 mg/kg body weight. The daily maintenance dose to be administered (once the steady state is reached) may be from 2.0 mg/kg body weight to 6 mg/kg body weight, e.g. from 4 mg/kg body weight to 6 mg/kg body weight. Therefore, according to the invention, the number of particles to be administered is measured by considering the amount of sultiame per particle and the dose per intake to be administered, in particular in view of the weight of the subject and the stage of the treatment.

The composition of the invention can be administered with or without food.

It is expected that the composition of the invention may allow to reduce the period of adaptation to treatment, which is currently about 5 to 6 days. Therefore, in some embodiments, with the composition of the invention, the daily initial dose should be administered during the first three days of treatment, i.e. during the first 72*h*, preferably during the first 48*h*. In another embodiment, it is not necessary to perform any initiation treatment with the composition of the invention.

Advantageously, the pharmaceutical composition of the invention is administered at most twice a day in the subject, namely once or twice a day preferably once a day or once every two days.

Advantageously, the subject is a person with swallowing disorder or a child, preferably an infant or a child under 7 years old. In some other embodiments, the subject with swallowing disorder is an elderly subject, e.g. of at least 65 years old.

Carbonic anhydrase inhibitors (CAIs) have been in clinical use for decades for the management of various disorders, including antitumor treatment. As member of the sulfonamide class with strong CA inhibitor, sultiame may have an anti-tumour activity, particularly in hypoxic tumors where the carbonic anhydrase (CA, EC 4.2.1.1) isoforms IX and XII are overexpressed. Thus, in an additional aspect, the invention relates to the use of the composition according to the invention, as an anti-tumoral agent, e.g. in the treatment of hypoxic tumors where the carbonic anhydrase (CA, EC 4.2.1.1) isoforms IX and XII are overexpressed. As mentioned above, the composition is to be administered via oral route. The dosage can be determined according to the criteria generally taken into account in the establishment of a treatment adapted to a patient such as, for example, the age or the body weight of the patient, the seriousness of his/her general condition, the tolerance to the treatment and the adverse effects noted.

In a further embodiment of the invention, the pharmaceutical composition of the invention, for use according to the invention, may be administered in combination with another treatment c, e.g. with another antiepileptics drug or with an anticancer drug (e.g. histone deacetylase inhibitors, alkylating agents, antimetabolite nucleosides, angiogenesis inhibitors, and immune checkpoint inhibitors), depending on the sought therapeutic effect (i.e. treatment of epilepsy or tumor).

The effective amount of this combination or the relative ratios of both active ingredients may vary upon the subject condition. As detailed earlier, the amount of each compound of the combination or of pharmaceutical composition containing such combination to be administered has to be determined by standard procedure well known by those of ordinary skills in the art. Physiological data of the patient (e.g. age, size, and weight) have to be taken into account to determine the appropriate dosage, so as a therapeutically effective amount of such combination will be administered to the patient. The pharmaceutical combination of the invention is more specifically for a simultaneous, separate or sequential administration, preferably for simultaneous administration, of said active ingredients.

The invention also relates to a pharmaceutical kit comprising the pharmaceutical composition in the form of particle of the invention, and a device suitable for distributing a pre-determined number or volume of said particle(s), wherein the pre-determined number of particles is preferably an integer from 1 and 25, preferably from 1 to 10 such as 1, 2, 3, 4 or 5.

EXAMPLES

This invention will be better understood in light of the following examples, which are provided for illustrative purposes only.

Example 1: Preparation of a Pharmaceutical Composition According to the Invention (ADV6769)

The prolonged release composition in the form of beads comprising sultiame is obtained in two steps:

1—the manufacturing of immediate release beads comprising sultiame by core layering of a suspension comprising sultiame onto neutral core (by spray-drying); and 2—the manufacturing of prolonged release beads comprising sultiame by coating with a prolonged release outer coating.

1—Preparation of the IR Beads

The suspension to be coated on the microcrystalline cellulose cores is prepared by mixing sultiame with the viscosity increasing agent and the surfactant in water under high speed stirring.

Then, resulting suspension is spray-dried on microcrystalline cellulose cores in a fluidized bed coater so as to obtain the immediate release bead (e.g. the pre-bead comprising the first layer). The composition is presented in Table 1.

TABLE 1

Composition of IR beads

| Ingredient | % Total composition |
|---|---|
| Purified water | — |
| Sultiame (API) | 66.8 |
| Microcrystalline cellulose sphere (Neutral core) | 10.8 |
| HPMC (Viscosity increasing agent/binding agent) | 15.7 |
| pegylated hydrogenated castor oil (Surfactant) | 6.7 |

2—Preparation of the PR Beads

After sieving, the IR beads previously obtained are coated with the coating suspension by spray-drying in a fluidized bed coater, so as to form the outer layer on the IR beads.

The coating suspension is obtained by mixing the hydrophobic polymer, the hydrophilic polymer, the plasticizer and the surfactant in a volatile solvent, e.g. a mixture of acetone, isopropyl alcohol and water, under stirring.

TABLE 2

Composition of PR beads

| Ingredient | % Total composition |
|---|---|
| IR bead | 80.0 |
| Ethylcellulose (Hydrophobic polymer) | 5.9 |
| Castor oil (Plasticizing agent) | 1.0 |
| pegylated hydrogenated castor oil (Surfactant) | 0.7 |
| Polyvinyl pyrrolidone (Hydrophilic polymer) | 12.4 |
| Acetone (Solvent) | — |
| Isopropyl alcohol (Solvent) | — |
| Purified water (Solvent) | — |
| Theoretical sultiam content (%) | 53.5 |

Example 2: In Vitro Dissolution Assay

Dissolution tests by UV monitoring were performed according to the European Pharmacopeia 01/2016:20903, with the following conditions:

Bath temperature: 37° C.
Stirring type: paddle
Stirring speed: 100 rpm
Dissolution medium: phosphate buffer 0.05 M at pH 6.8, Dissolution volume: 900 mL UV detection—wavelength: $\lambda$=245 nm
Cell path lenght: 1 cm
Test run: 10 beads as obtained in example 1

The results are shown in FIG. 1. FIG. 1 also shows the in vitro dissolution profile for Ospolot® film-coated tablet obtained in the same dissolution conditions.

The in vitro dissolution assay was repeated in different acid pHs. Of note, the in vitro dissolution curve obtained for the composition of the invention are essentially the same at 1.2 and 4.5 as in pH 6.8. Acidic pHs have thus no effect on the in vitro dissolution release rate of sultiame in the composition of the invention.

Example 3: Randomised, Controlled, Parallel Groups, Open Label Clinical Study to Explore the Pharmacokinetics Profile, Pharmacodynamics, Safety and Tolerability of the Composition of the Invention (Named ADV6769) as Compared to the Reference Product (Ospolot®), in Healthy Subjects Development Phase: Phase I Primary Objective:

To characterize the pharmacokinetics (PK) of sultiame, including its release profile from the formulation of the Invention (ADV6769), in plasma after oral administration of single doses of 50, 200 and 400 mg of ADV6769 versus 200 mg of Ospolot® in healthy subjects.

Study Design:

Randomised, controlled, parallel groups, open label study with three doses of ADV6769 (50, 200 and 400 mg) or one dose of Ospolot® (200 mg) and 2 parts (Part A randomised and Part B).

Eligible subjects will be randomized in one of the 3 following treatment arms: ADV6769 50 mg, ADV6769 200 mg or Ospolot® 200 mg (Part A).

The following data of these 3 treatment arms will be reviewed before enrolment of eligible subjects in the treatment arm ADV6769 400 mg (Part B).

Study period: period during which a subject will be admitted to the unit for at least 72 hours, from Day-2 evening to Day 2 (at least 36 hours) after the administration of a single dose of one of the study products.

End of study: 29th days after the administration of the study product.

Study constraints and restrictions: no beverages containing alcohol, coffee, fruits or herbal tea and no smoking during the study periods, fasting period from 10 hours before until 4 hours after IMP administration, standardised food during hospitalisation, from Day−2 to Day2 t36 h. The recommended methods of contraception must be used during the study until 33 days after study treatment for female subjects and 93 days after study treatment for male subjects.

Study Population:

Subjects number: 24 subjects with 6 subjects per arm

Main Eligibility Criteria:

Healthy adult subject, female or male, from 18 to 55 years of age, with a BMI between 18 and 27 kg/$m^2$ Subject without medical major history or chronic treatment Study Products:

Active study products: ADV6769, prolonged-release granule formulation, for oral administration at three doses (50 mg, 200 mg and 400 mg).

Marketed oral tablet of Ospolot® 200 mg.

Administration: Administration of a single oral dose for each study product (ADV6769 50, 200 and 400 mg, Ospolot® 200 mg).

Study Endpoints:

Main Assessment Criterion

Pharmacokinetics

Main PK parameters of sultiame for ADV6769 formulation and Ospolot® calculated using non-compartmental method:

Area under the curve up to time t (AUC0-t)

Maximal Concentration (Cmax)

Time to reach Cmax (Tmax)

Statistical Analysis

Plasma concentrations will be summarized by treatment and overtime, and individual and mean±SD concentrations will be tabulated and presented graphically.

Plasma PK parameters will be analyzed using a traditional non-compartmental approach, by treatment (ie. for each of the 3 doses of ADV6769 and Ospolot® 200 mg), including the following parameters:

Area under concentration curve up to time t(AUC0-t): will be calculated with the trapezoidal and log-trapezoidal rules.

Maximal concentration (Cmax)

Time to reach Cmax (Tmax)

Results

Table 3 summarizes the pharmacokinetics data of sultiame in plasma for the PK population, for ADV6769 at the dose 50, 200 and 400 mg and Ospolot® at the dose 200 mg. As it can be seen, the composition of the invention (ADV6769) provides a prolonged release of sultiame in vivo characterized by a significant higher Tmax and a lower Cmax as compared to the drug reference (Ospolot®) when administered at a dose corresponding to 200 mg of sultiame.

TABLE 3

Results of pharmacokinetics study

| Parameter | Type of data | Statistics | ADV6769 50 mg (N = 6) | ADV6769 200 mg (N = 6) | ADV6769 400 mg (N = 6) | Ospolot ® 200 mg (N = 6) |
|---|---|---|---|---|---|---|
| Cmax | Raw data | N (missing) | 6 (0) | 6 (0) | 6 (0) | 6 (0) |
| (μg/mL) | | Mean (SD) | 0.026 (0.042) | 0.209 (0.089) | 0.660 (0.265) | 1.763 (0.911) |
| | | Median | 0.000 | 0.242 | 0.727 | 1.825 |
| | | Min; Max | 0.000; 0.094 | 0.077; 0.295 | 0.236; 0.940 | 0.455; 3.172 |
| | | Q1; Q3 | 0.000; 0.064 | 0.123; 0.275 | 0.474; 0.859 | 1.203; 2.100 |
| Tmax (h) | Raw data | N (missing) | 2 (4) | 6 (0) | 6 (0) | 6 (0) |
| | | Mean (SD) | 24.000 (16.971) | 48.000 (13.145) | 36.167 (25.802) | 2.333 (0.816) |
| | | Median | 24.000 | 48.000 | 42.000 | 2.500 |
| | | Min; Max | 12.000; 36.000 | 36.000; 72.000 | 5.000; 72.000 | 1.000; 3.000 |
| | | Q1; Q3 | 12.000; 36.000 | 36.000; 48.000 | 8.000; 48.000 | 2.000; 3.000 |
| AUC0-t | Raw data | N (missing) | 2 (4) | 6 (0) | 6 (0) | 6 (0) |
| (h*ug/mL) | | Mean (SD) | 0.220 (0.221) | 13.358 (7.617) | 40.721 (23.549) | 27.279 (13.049) |
| | | Median | 0.220 | 13.318 | 40.998 | 29.741 |
| | | Min; Max | 0.064; 0.376 | 1.943; 21.893 | 7.415; 71.616 | 7.134; 43.253 |
| | | Q1; Q3 | 0.064; 0.376 | 9.136; 20.544 | 27.013; 56.284 | 17.536; 36.269 |

The invention claimed is:

1. A prolonged-release pharmaceutical composition for oral administration of sultiame in the form of particles, wherein the particles have a maximal particle size of at most 3000 μm and comprise:

a core, having a particle size ranging from 600 μm to 1000 μm, which is devoid of sultiame, a first layer surrounding the core, which comprises sultiame, and an outer layer surrounding said first layer and providing prolonged-release of sultiame, the amount of sultiame being from 0.5 mg to 5.0 mg per particle, and wherein, when orally administered in one daily dose of 200 mg to healthy adult subjects under fasting conditions, the prolonged-release pharmaceutical composition provides a pharmacokinetic profile for sultiame having the following features:

(i) a median $T_{max}$ of at least 36 hours;

(ii) a mean $C_{max}$ of less than 0.3 μg/mL; and (iii) a mean $AUC_{0-t}$ of less than 22 h*μg/mL.

2. The prolonged-release pharmaceutical composition of claim 1, wherein the core is made of an inert component selected from cellulose, microcrystalline cellulose or combinations thereof.

3. The prolonged-release pharmaceutical composition of claim 1, wherein the first layer further comprises a viscosity increasing agent and/or a surfactant.

4. The prolonged-release pharmaceutical composition of claim 1, wherein the core is made of an inert component selected from polysaccharides, silica, calcium carbonate, magnesium carbonate, sugar, polyol, or mixtures thereof.

5. The prolonged-release pharmaceutical composition of claim 1, wherein:

no more than 20% of sultiame initially present in the composition is released within 1 h;

from 30% to 60% of sultiame initially present in the composition is released within 6 h; and at least 80% of sultiame initially present in the composition is released within 14 h, when the pharmaceutical composition is subjected to an in vitro dissolution assay at pH 6.8 according to European Pharmacopeia 01/2016:20903.

6. The prolonged-release pharmaceutical composition of claim 1, wherein from 70% to 100% of the particles, by weight, have a particle size from 1000 μm to 3000 μm.

7. The prolonged-release pharmaceutical composition of claim 1, wherein the amount of sultiame per particle is from 0.5 mg to 2.5 mg.

8. The prolonged-release pharmaceutical composition of claim 1, wherein the outer layer comprises at least one hydrophilic polymer and at least one hydrophobic polymer, and wherein the weight ratio of the at least one hydrophobic polymer to the at least one hydrophilic polymer is from 1.5 to 3.

9. The prolonged-release pharmaceutical composition of claim 8, wherein the at least one hydrophilic polymer is polyvinylpyrrolidone and the at least one hydrophobic polymer is ethylcellulose.

10. The prolonged-release pharmaceutical composition of claim 8, wherein the outer layer further comprises a plasticizer and/or a surfactant.

11. A method of treating epilepsy in a subject comprising administering a prolonged-release pharmaceutical composition of claim 1 to the subject.

12. The method of claim 11, wherein the subject is a child, an infant, and/or a subject with swallowing disorder.

13. The method of claim 11, wherein the prolonged-release pharmaceutical composition is administered at most twice a day in the subject, or once daily or once every two days.

14. The method of claim 11, wherein the daily dose of sultiame is from 0.1 mg/kg to 10.0 mg/kg.

15. The prolonged-release pharmaceutical composition of claim 1, wherein the core is in a shape of a sphere.

16. The prolonged-release pharmaceutical composition of claim 9, wherein the outer layer further comprises castor oil as a plasticizer and pegylated hydrogenated castor oil as a surfactant.

17. The prolonged-released pharmaceutical composition of claim 1, wherein:

the core is a spherical core made of microcrystalline cellulose and having a particle size ranging from 650 μm to 900 μm, the first layer comprises sultiame in an amount from 0.5 mg to 2.5 mg, hydroxypropyl methyl cellulose (HPMC) as a viscosity increasing agent and pegylated hydrogenated castor oil as a surfactant, and the outer layer comprises ethylcellulose as a hydrophobic polymer and polyvinylpyrrolidone (PVP) as a hydrophilic polymer in a weight ratio of ethylcellulose to PVP of 1.5 to 3, castor oil as plasticizer and pegylated hydrogenated castor oil as surfactant.

18. The prolonged-released pharmaceutical composition of claim 1, wherein the particles are obtained by spray-drying in a fluidized bed coater.

* * * * *